US006187299B1

(12) United States Patent
Wimmer et al.

(10) Patent No.: US 6,187,299 B1
(45) Date of Patent: Feb. 13, 2001

(54) LIQUID COMPOSITION USED FOR DISSOLVING FINGERNAIL POLISHES

(75) Inventors: Eric P. Wimmer, Princeton; Thomas R. Candia, Cedar Grove; Hong Sajonz, Edison, all of NJ (US); Ronnie Mui, Reading, PA (US)

(73) Assignee: Tevco, Inc., South Plainfield, NJ (US)

( * ) Notice: Under 35 U.S.C. 154(b), the term of this patent shall be extended for 0 days.

(21) Appl. No.: 09/416,573

(22) Filed: Oct. 12, 1999

(51) Int. Cl.⁷ ............................... A61K 7/04; A61K 6/00
(52) U.S. Cl. ................................. 424/61; 424/401
(58) Field of Search ....................... 424/61, 401

(56) References Cited

U.S. PATENT DOCUMENTS 5,290,555 * 3/1994 Guthauser et al. .................. 424/401

FOREIGN PATENT DOCUMENTS

01160908 * 6/1989 (JP) .
30 09 763 * 6/1989 (DE) .

* cited by examiner

Primary Examiner—Thurman K. Page
Assistant Examiner—S. Tran
(74) Attorney, Agent, or Firm—Bucknam and Archer

(57) ABSTRACT

A liquid composition used for dissolving fingernail polishes contains three non-miscible liquid phases which, when the composition is left still, are superimposed one on the other. The upper phase is oily. The intermediate phase is the solvent phase and contains a solvent immiscible with water and a small amount of a solvent miscible with water. The composition contains 8–40% of water and at least one polymeric glycol. By agitation, an emulsion is formed which is applied on the fingernails.

16 Claims, No Drawings

LIQUID COMPOSITION USED FOR DISSOLVING FINGERNAIL POLISHES

FIELD OF THE INVENTION

The present invention relates to novel cosmetic compositions used for dissolving fingernail polishes. In particular, the invention relates to novel liquid compositions which dissolve fingernail polishes and which are constituted by three liquid phases, not miscible, which are superimposed one over the other when the compositions remain still.

BACKGROUND OF THE PRIOR ART

Solvents for fingernail polishes have been known for many years. The most classical solvents are based on an organic solvent which has a good dissolving power for the fingernail polishes and which is sufficiently volatile such as acetone or ethyl acetate. However, for the reasons of protection of the individuals, protection of the environment and most significant for the purpose of avoiding the danger of inflammation, air pollution and the risks of intoxication due to the vapors, it is desirable to decrease the quantity of these solvents in the nail polish removers.

In addition, these known solvents being applied on the fingernails are not free of toxic action to the organism. Actually they have substantial delipidating action and a dehydrating action of the nails. Some of these solvents as acetone penetrate into the organism through the skin and are known to be toxic to the liver. Several compositions which dissolve fingernail polishes have been proposed to decrease these drawbacks, but none of them offers all the properties which are desirable for solvents of fingernail polishes. Indeed compositions being used as solvents must offer simultaneously a good solvent power for the fingernail polishes, a good speed of evaporation, a very good harmlessness with respect to the constituents of the nails and the skin and must be free of toxicity by contact or inhalation.

A solvent made up of three phases has been described in Japanese Patent application JP 1-160908. It is constituted by an upper phase which is oily, a lower phase based on water and acetone and an intermediate phase based on propylene carbonate mixed with a hydrocarbon solvent and also with acetone. On one hand the presence of an oily substance in the upper phase allows to prevent the solvent from evaporating, but on the other hand this composition has the drawback of containing propylene carbonate, a solvent which is not sufficiently volatile. Due to this fact, the composition remains on the fingers for too long a period of time and the risks of damaging surfaces of plastic materials or paintings with which they would come into contact are increased.

This composition of the prior art contains also hydrocarbon solvents such as toluene or xylene which are considered very dangerous. In addition to these solvents, acetone, the drawbacks of which are known, is indispensable and is present in a substantial amount.

There is, therefore, a need of a composition to dissolve the fingernail polishes which is free of the drawbacks of the compositions of the prior art.

SUMMARY OF THE INVENTION

The object of the present invention is to provide a new liquid composition with three non-miscible liquid phases capable of dissolving the fingernail polish characterized by the fact that it comprises:

from 9.8% to 30% by weight of at least one oil a) selected from the group consisting of oils which are liquid in a temperature range from 40° F. to 120° F.;

from 20% to 56% by weight of at least one solvent b) for the fingernail polishes, not miscible with water and which does not fall into the class of hydrocarbons;

from 0.1% to 24% by weight of at least one solvent c) for the fingernail polishes miscible with water, the total weight of the solvents b) and c) being from 20.1% to 70% by weight;

from 8% to 40% by weight of water; and from 8% to 35% preferably from 10% to 35% by weight of at least one polymeric glycol d) having an average molecular weight in the range from 200 to 1200.

When the composition is left still, it is in the form of three liquid phases superimposed one on the other.

Simply by agitation, prior to being used, the composition is obtained in the form of an emulsion which is applied on the fingernail polishes. This emulsion permits to eliminate the fingernail polish while in the same time conditioning the nails and cuticles.

The upper phase of the composition is oily. This phase amounts preferably from 10% to 30%, in particular 15% to 25% by weight with reference to the weights of the three phases of the composition. This phase prevents the solvent to evaporate and at the same time furnishes the useful fatty constituents for the skin and the fingernails.

The upper phase is constituted by 98% up to 100% by weight of at least one oil a) which is liquid in the temperature range from 40° F. to 120° F. and which is cosmetically acceptable. These oils must in addition be very little compatible with the solvents of the intermediate phase and must exhibit a density lower with respect to the latter. The useful oils are selected from the group constituted by mineral oils such as the mineral oil sold under the tradename "DUOPRIME OIL 70" by the firm Lyon Dell Lubricants and vegetable oils such as the soja oil.

The intermediate phase is a solvent phase. It amounts preferably to 40% to 70% and more specifically 40% to 55% by weight with respect to the total weight of the three phases of the composition. It is constituted mainly by at least one organic solvent b) of the fingernail polishes, the solvent being not miscible with water and being other than a hydrocarbon, and at least one polymeric glycol e).

The single solvent or more solvents b) amount in this phase from 50% to 80%, preferably 65% to 80% of the weights of the combination of solvents and polymeric glycols.

The single polymeric glycol or the several polymeric glycols amount from 20% to 50%, preferably 20% to 35% of the weights of the combination of solvents and polymeric glycols in this intermediate phase.

The solvents b) which are not miscible with water and which are known for the purpose of dissolving the fingernail polishes to be used in the composition of the present invention are selected from the group consisting of alcohols, esters (carbonates not included) ethers, ketones, glycols and their mixtures.

The advantage of using these solvents resides in the fact that they are not toxic as the hydrocarbon solvents and particularly aromatic hydrocarbons. By way of examples of the solvents which are suitable there may be mentioned ethyl acetate, butyl acetate, propyl acetate, amyl acetate and their mixtures.

Together with one or more of the solvents for the fingernail polishes, the intermediate phase contains at least one polymeric glycol which serves the function of being a moisturizer for the skin and as a stabilizer of the system and which has an average molecular weight from 200 to 1200. Preferably one selects substances from the group constituted by polypropylene-glycols and polyethylene-glycols.

By way of examples of these glycols, one may mention polypropylene-glycol P-425 and polyethylene-glycol E200.

The lower phase is an aqueous phase. This phase constitutes preferably from 20% to 40% and particularly from 35% to 40% by weight of the combination of the three phases.

In addition to water the aqueous phase contains one or more solvents c) for the fingernail polishes miscible with water. Useful solvents of this type are selected from the group consisting of alcohols, esters (not included carbonates) ethers, ketones, glycols and their mixtures soluble in water.

The aqueous phase also contains one or more polymeric glycols d). The polymeric glycols are selected among those substances which are used in the intermediate phase of the composition. They may be the same or different from the polymeric glycols used in the intermediate phase.

It should be noted that the polymeric glycol is an essential component and this substance is present in the intermediate phase but may also be present in the aqueous phase.

In general, the aqueous phase contains from 40% to 99.5% by weight of water, from 0.5 to 60% by weight of the solvent and from 0 to 60% by weight of the polymeric glycol with respect to the total weights of these three compounds. Preferably the aqueous phase contains from 60% to 90% by weight of water, from 10% to 40% by weight of the solvent and from 0% to 15% by weight of the polymeric glycol. The water allows the hydration of the fingernails and the cuticles. Preferably deionized water or distilled water is used. The solvents used in this phase increase also the solvent power of the composition. Preferred solvents are diacetone-alcohol, acetone, ethanol, isopropanol, butanol.

The preferred polymeric glycols in this phase are polypropylene glycol P-425 and polyethylene glycol E 200.

In addition to the main ingredients described hereinabove, one may add in the composition substances such as perfumes, coloring materials, UV filters and preservative agents so that the composition becomes more attractive and also the physical and chemical properties are improved. These materials are selected among the substances normally used in the cosmetic field.

Each phase of the composition may more particularly be colored by means of coloring agents soluble solely in one of the phases and with different colors. When the composition is still, the fact that one phase is superimposed over the other makes the appearance more pleasant. As the coloring agents, one may mention for instance the substances known as "D & C" and "F & D and C", colorants, such as examples D & C Violet #2, F, D and C Blue #1, D & C #33, D & C Red #17.

In general the composition contains from 0 to 0.6% of coloring material soluble in the oils, 0 to 1.4% of coloring materials soluble in the solvents and between 0 and 0.8% of coloring materials soluble in water and the solvent of the aqueous phase.

The perfumes amount in general to 0 up to 0.007% by weight of the composition. Essentially they are added in the oily phase and in the aqueous phase. They may totally neutralize the odors of the solvents and develop a very agreeable fragrance.

The UV filters and the preservatives amount in general respectively from 0 to 0.014% by weight and 0 to 0.014% by weight of the composition. As UV filters one for example may mention benzophenone-1 or -4 and as preservatives methyl paraben, propyl paraben, butyl paraben.

When one wishes to use the composition, one must shake it. In this manner, a brown emulsion is formed which one applies on the fingernails covered with the polish which must be eliminated. The latter is eliminated very easily and at the same time the nails and the cuticles are conditioned by the composition of the invention. When the composition is allowed to be still, the three phases separate one from the other, one is superimposed again on the other and the composition reacquires its original tri-color appearance.

The following examples illustrate but are not limiting the invention:

EXAMPLE 1

A nail remover composition is prepared according to the invention constituted by the following materials (the values are expressed by parts per weights):

| | |
|---|---:|
| Mineral oil ("Duoprime Oil 70") | 19.621 |
| Ethyl Acetate | 29.153 |
| Deionized water | 24.470 |
| Acetone | 12.019 |
| P425 PPG (polypropylene glycol) | 14.634 |
| "D.&C. yellow #11" | 0.075 |
| "F.D.&C. green #6" | 0.009 |
| "D.&C. red #33" | 0.007 |
| Benzophenone-1 (UV stabilizer) | 0.006 |
| Benzophenone-4 (UV stabilizer) | 0.004 |
| Lilac fragrance | 0.002 |
| Total | 100.000 |

Prior to the first use of the composition, the distribution of the components in the three phases superimposed one on the other is the following:

| Top Layer: Oil Phase | Middle Layer: Solvent Phase | Bottom Layer: Aqueous Phase |
|---|---|---|
| Mineral Oil 70: 99.60% | Ethyl Acetate: 66.56% | Deionized Water: 67.04% |
| "D.&C. Yellow #11: 0.38% | P 425 PPG: 33.41% | Acetone 32.93%/ |
| Benzophenone-1(UV Stabilizer)0.01% | "F. D. & C. Green #6: 0.02% | "D. &C. Red #33": 0.02% |
| Lilac fragrance: 0.01% | Benzophenone-1(UV Stabilizer): 0.01% | Benzophenone-4(UV Stabilizer): 0.01% |
| Stand Alone Total 100% | Stand Alone Total 100% | Stand Alone Total 100% |
| Final Formula 19.7% | Final Formula 43.8% | Final Formula 36.5% |

EXAMPLE 2

A nail remover composition is prepared according to the invention constituted by the following materials (the values are expressed by parts per weights):

| | |
|---|---:|
| Mineral oil ("Duprime Oil 70") | 19.621 |
| Ethyl Acetate | 33.533 |
| Deionized water | 24.470 |
| Acetone | 8.369 |
| P425 PPG | 10.253 |
| PEG (polyethylene glycol)(MW:209) | 3.650 |
| "D.&C. yellow #11" | 0.075 |
| "F.D.&C. green #6" | 0.009 |
| "D.&C. red #33" | 0.007 |
| Benzophenone-1 (UV stabilizer) | 0.006 |
| Benzophenone-4 (UV stabilizer) | 0.004 |
| Lilac fragrance | 0.002 |
| | 100.000 |

For the purpose of removing the fingernail polish, one shakes the dissolving composition and obtains an emulsion which has dissolving power and which color is brown. The emulsion is applied on the fingernails in the conventional manner.

EXAMPLE 3

A nail remover composition is prepared according to the invention constituted by the following materials (the value are expressed by parts per weights):

| | |
|---|---:|
| Mineral oil ("Duprime Oil 70") | 19.621 |
| Ethyl acetate | 29.153 |
| Deionized water | 28.120 |
| Acetone | 8.369 |
| P-425 PPG | 4.380 |
| PEG-200 | 10.253 |
| "D.&C. yellow #11" | 0.075 |
| "F.D.&C. green #6" | 0.009 |
| "D.&C. red #33" | 0.007 |
| Benzophenone-1 (UV stabilizer) | 0.006 |
| Benzophenone-4 (UV stabilizer) | 0.004 |
| Lilac fragrance | 0.002 |
| Total | 100.000 |

Process for the Preparation of the Composition Used for Dissolving Fingernail Polishes In general the three phases are separately prepared and then are blended together.

Preparation of the Top Layer: Oil Phase

In a clean tank Mineral Oil 70 in the amount of 98–99.8%, preferably 99.60% is mixed at low speed with D&C Yellow #11 0.38%. When the solution is uniform 0.01% Benzophenone as a UV filter is added and then 0.01% of a Lilac Fragrance. The total of the preferred amounts is 100%. The mixture is mixed on slow to medium speed for 15 mins.

Preparation of the Middle Layer: Solvent Phase

A solvent not miscible with water, for instance ethyl acetate, 65%–80%, preferably 76.56% is used. The mixer is turned at slow speed. Then polypropylene glycol, P425PPG, in the amount of 20–50%, preferably 23.41% is added. Then FD&C Green #6 0.02% is added. When the solution is uniform, Benzophenone 0.01% is added. The mixture is mixed at a slow to medium speed for 15 mins. The total of the preferred amounts is 100%.

Preparation of the Bottom Layer: Aqueous Phase

In a clean plastic tank deionized water in the amount of 60–90% preferably 67.04%, is mixed at low speed with D&C Red #33 0.02%, PEG 10.00%, Acetone 0.5–40%, preferably 22.93%, Benzophenone 0.01%. The total when the different components are used in the preferred amounts, is 100%.

What is claimed is:

1. A nail polish removing liquid composition having three liquid and immiscible phases, said phases being superimposed one on the other when the composition is still, said composition consisting essentially of:

from 9.8% to 30% by weight of at least an oil a) selected from the group consisting of mineral oils and vegetable oils, which are in liquid form at a temperature ranging from 40° F. to 120° F.;

from 20% to 56% by weight of at least one removing nail enamel solvent b) which is immiscible with water, and which is other than a hydrocarbon;

from 0.1% to 24% by weight of at least one removing nail enamel solvent c) which is miscible with water, the total weight of solvents b) and c) in the composition being from 20.1% to 70% by weight;

from 8 to 40% by weight of water; and from 8% to 35% by weight of at least one glycol polymer d) selected from the group consisting of polyethylene-glycols and polypropylene-glycols, which having an average molecular weight in the range of 200 to 1200.

2. The composition according to claim 1, which, when still, has a top phase, a middle phase and a bottom phase, said top phase being oily, said middle phase being a solvent phase, said bottom phase is an aqueous phase, said top phase being 10 to 30%, said middle phase being 40 to 70%, said bottom phase being 20 to 40% of the total weight of said three phases of said composition.

3. The composition according to claim 2, wherein said oily top phase comprises from 98% to 100% by weight of at least one oil (a).

4. The composition according to claim 2, wherein said middle phase comprises essentially from 50% to 80% by weight of at least one nail polish remover solvent (b) which is immiscible with water and from 20% to 50% by weight of at least one of said glycol polymer (e).

5. The composition according to claim 4, wherein said solvent (b) immiscible with water is a member selected from the group consisting of alcohols, esters other than carbonates, ethers, ketones, glycols and mixtures thereof.

6. The composition according to claim 5, wherein said solvent b) is a member selected from the group consisting of ethylacetate, butylacetate, propylacetate, amylacetate and mixtures thereof.

7. The composition according to claim 1, wherein said bottom aqueous phase comprises from 40% to 99.5% by weight of water, from 0.5 to 60% by weight of at least one nail polish remover solvent c) which is miscible with water and from 0 to 60% by weight of at least one glycol polymer (d).

8. The composition according to claim 7, wherein said solvent c) miscible with water is a member selected from the group consisting of alcohols, esters other than carbonates, ethers, ketone, glycols and mixtures thereof.

9. The composition according to claim 8, wherein the water miscible solvent c) is a member selected from the group consisting of acetone, diacetone-alcohol, ethanol, isopropanol and butanol.

10. The composition according to claim 1, wherein said vegetable oil is soja oil.

11. The composition according to claim 1, which comprises at least one additive which is a member selected from the group consisting of preservatives, coloring agents, UV filters and fragrances.

12. The composition according to claim 11, wherein coloring agents in the amount of 0 to 0.6% are soluble in said oily phase; coloring agents soluble in said solvents b) are in the amount of 0 up to 1.4%, coloring agents soluble in water and water miscible solvents are in the amount of 0 to 0.8%, the UV filters are in the amount of 0 to 0.014%, the fragrances are in the amount of 0 to 0.007% and the preservatives are in the amount of 0 to 0.014% by weight.

13. The composition according to claim 11, wherein the oil phase a) contains from 0 to 0.6% by weight of oil soluble coloring agents, from 0 to 0.01% by weight of UV filters, and from 0 to 0.01% by weight of a fragrance.

14. The composition according to claim 11, wherein the middle solvent phase contains from 0 to 1.4% by weight of solvent soluble coloring agents and 0 to 0.01% by weight of UV filters.

15. The composition according to claim 11, wherein said bottom aqueous phase contains from 0 to 0.8% by weight of water soluble coloring agents, from 0 to 0.01% by weight of UV filters, from 0 to 0.01% by weight of fragrance and from 0 to 0.25% by weight of preservative.

16. A process for the preparation of a nail polish removing liquid composition having three liquid and immiscible phases, said phases being superimposed one on the other when the composition is still, said composition comprising;
  from 9.8% to 30% by weight of at least an oil (a) selected from the group consisting of mineral oils and vegetable oils, which are in liquid form at a temperature ranging from 40° F. to 120° F.;
  from 20% to 56% by weight of at least one removing nail enamel solvent (b) which is immiscible with water, and which is other than a hydrocarbon;
  from 0.1% to 24% by weight of at least one removing nail enamel solvent (c) which is miscible with water,
  the total weight of solvents (b) and (c) in the composition being from 20.1% to 70% by weight;
  from 8 to 40% by weight of water; and 8 to 35% by weight of at least one glycol polymer (d) selected from the group consisting of polyethlene-glycols and polypropylene-glycols, which having an average molecular weight in the range of 200 to 1200 which consists essentially of the steps of separately preparing said three liquid phases and then blending said phases.

* * * * *